United States Patent [19]

Kamen

[11] Patent Number: 4,680,462
[45] Date of Patent: Jul. 14, 1987

[54] FLUID DROP DETECTION SYSTEM
[75] Inventor: Dean L. Kamen, Bedford, N.H.
[73] Assignee: Baxter Travenol Laboratories, Inc., Deerfield, Ill.
[21] Appl. No.: 680,487
[22] Filed: Dec. 11, 1984
[51] Int. Cl.$^4$ ............................................. G01V 9/04
[52] U.S. Cl. ................................. 250/222.1; 604/253
[58] Field of Search .................. 250/221, 222.1, 222.2, 250/561, 564, 565; 356/433, 436; 377/53; 604/253

[56] References Cited
U.S. PATENT DOCUMENTS

| | | | |
|---|---|---|---|
| 3,563,090 | 2/1971 | Deltour | 73/194 |
| 4,038,982 | 8/1977 | Burke et al. | 128/214 |
| 4,105,028 | 8/1978 | Sadlier et al. | 128/214 |
| 4,125,779 | 11/1978 | Malinowski | 340/630 |
| 4,225,791 | 9/1980 | Kompelien | 250/574 |
| 4,431,425 | 2/1984 | Thompson et al. | 604/246 |
| 4,498,901 | 2/1985 | Finch | 604/253 X |

Primary Examiner—Eugene R. LaRoche
Assistant Examiner—Steven J. Mottola
Attorney, Agent, or Firm—B. Surstein; K. Pierce; P. Flattery

[57] ABSTRACT

A system detecting the presence of successive drops of fluid in a fluid path has a system input for connection to a photoelectric transducer so situated as to have a change in electrical output on the presence of a drop in the fluid drop path. The system includes an arrangement for storing a quantity related to the value of the photoelectric transducer output in the absence of a drop. The quantity stored can then be compared with the present value of the output of the photoelectric transducer, and in the event of a sufficient difference, an output may be provided. In a preferred embodiment, the output signal itself may be used to disconnect the storage system from receiving input information that pertains to the presence rather than the absence of a drop.

11 Claims, 1 Drawing Figure

FLUID DROP DETECTION SYSTEM

DESCRIPTION

1. Technical Field

The present invention relates to devices for detecting the essence of a drop in a drip chamber or other similar part of a medical infusion system. In particular, the invention relates to detection devices of the type utilizing an electrically powered light source and corresponding photoelectric transducer.

2. Background Art

Fluid drip detectors must be designed to function in a difficult environment. Typically a drop of fluid is not capable of causing a large change in amplitude in the light transmitted along a path transverse to the fluid drop path. Furthermore, ambient light conditions are subject to violent and rapid change, and so may give rise to spurious signals. A variety of approaches are reflected in the art to this problem. U.S. Pat. No. 4,321,461, issued for an invention of Walter et al., discloses a system using a pulsed infra-red radiation emitter and receiver pair including a phototransistor which is subject to negative feedback to attempt to stabilize the system. A pulse system in a device for detection of emboli is disclosed in U.S. Pat. No. 4,280,495 issued for an invention of Lampert. Another feedback system is used to stabilize a light detection device by regulating the output of the light emitter, and is disclosed in U.S. Pat. No. 4,314,484, issued for an invention of Bowman.

DISCLOSURE OF INVENTION

The present invention provides a system for detecting the presence of successive drops of fluid in a fluid path, and has a system input for connection to a photoelectric transducer so situated as to have a change in electrical output on the presence of a drop in the fluid drop path. The system includes an arrangement for storing a quantity related to the value of the photoelectric transducer output in the absence of a drop. The quantity stored can then be compared with the present value of the output of the photoelectric transducer, and in the event of a sufficient difference, an output may be provided. In a preferred embodiment, the output signal itself may be used to disconnect the storage system from receiving input information that pertains to the presence rather than the absence of a drop.

DESCRIPTION OF SPECIFIC EMBODIMENT

Figure 1A:
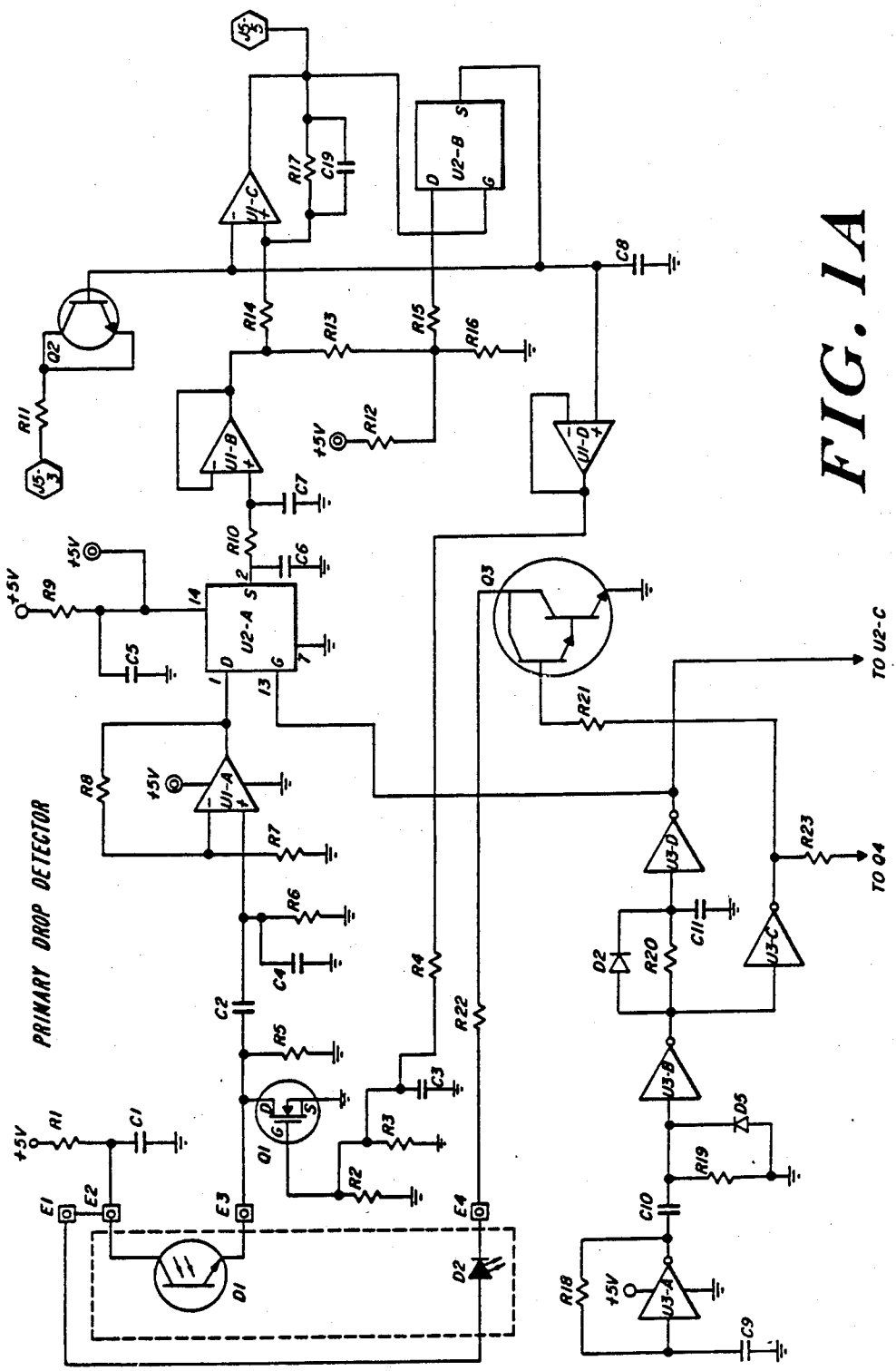

The foregoing and other features of the invention may be further understood by reference to the accompanying drawing, which presents in FIGS. 1A and 1B a schematic diagram of a preferred embodiment. Typical values for components are as follows. C5, 10 microfarads; C6, 0.01 microfarads; C7, 0.001 microfarads; C8, 0.027 microfarads; C10, 0.001 microfarads; C11, 100 picofarads; C19, 0.1 microfarads; R9, 68 ohms; R10, 100k ohms; R11, 100 ohms; R12, 10 megohms; R13, 51 k ohms; R14, 4700 ohms; R15, 1 megohm; R16, 1 megohm; R17, 1 megohm; R18, 300k ohms; R19, 22k ohms; R20, 100k ohms; R21, 4700 ohms; and R23, 4700 ohms.

The circuit operates as follows. D2 is a light emitting diode and is given a pulse at about 1 kilohertz frequency and of about 30 microseconds duration. The signal is delivered from Q3 over R22. (All resister values shown in the schematic are in ohms, and all capacitance values are in microfarads.) U3 is a six section Schmidt inverter-buffer, such as type 74C914. Pulse frequency is determined by values of R18 and C9 in the relaxation oscialator circuit associated with U3-A. The output of the oscillator is differentiated by C10 and clipped by D5 and subjected to buffering by U3-B to yield a negative pulse at the output of U3-B. The combination C11 and R20 produce a delay of approximately 15 microseconds at the input of U3-D, although the pulse ends at the same time as that at the output of U3-B. Consequently, the output of U3-D is a clean positive pulse of 15 microseconds duration that commences 15 microseconds after commencement of the 30 microsecond pulse at the output of U3-B. The 30 mircosecond pulse is inverted by U3-C and fed into Q3 to drive D2.

The shorter 15 microsecond pulse is used to gate the amplified signal from photodiode D1. When D1 is illuminated by D2, the output of D1 is subjected to a variety of filtering including high frequency filter C4 and high pass filter C2. U1 is a four section op-amp, such as type TLC274. U1-A is configured to give a gain of approximately 20 to gate U2-A, which is typically a part of type 4016. Owing to the signal on pin 13 of U2-A, conduction between pin 1 and pin 2 occurs only beginning approximately 15 microseconds after D2 has turned on from each pulse. This period of time is sufficient to permit transients in the system to die down. The output of U2-A is run through low-pass filter network including C6 and C7. Consequently the input to U1-B is indicative of the dc light level from photodiode D1.

U1-B is arranged as a voltage follower to provide current gain into the resistor network including R12 through R16. C8 is used to store a signal representative of the dc light level from photodiode D1 in the absence of a drop. In particular, R13 and R16 form a voltage divider, so that at their junction is present a signal of approximately 95% of the amplified and filtered photodiode output. This voltage is impressed on C8 via isolation resistor R15 and gate U2-B. As will be discussed in further detail below, the gate of U2-B is connected to the system output, so that C8 is disconnected from the signal whenever the output indicates the presence of a drop. In this manner, C8 stores 95% of the amplified and filtered photodiode output, but disregards any change when a drop is present. The node at C8 is therefore one input to comparator U1-C, which receives another input equal to 100% of the amplified and filtered photodiode output. In the event of a drop of more than 5% in the amplified and filtered photodiode output, the output of U1-C will go low. Consequently node J5-5 has on it an output that will go low each time the filtered photodiode output drops more than 5%. Resistor R17 provides positive feedback to the comparator circuit, and C19 may be optionally connected in parallel with R17. Since the output of U1-C goes low in the presence of a drop, its output is used to gate off the path between R15 and C8 whenever a drop has been detected, so that C8, in the manner discussed above, stores a signal that is 95% of the amplified and filtered photodiode output only in the absence of a drop.

In the event of streaming, or if the light emitting diode or photodiode is disconnected, or in any other event of sustained reduction of output it will be necessary to reset the voltage on C8. The resetting operation is accomplished at node J5-3, which when grounded will cause the discharge of C8 through Q2 (here arranged as a diode) and R11. The effect of the reset is to set the light level in the absence of a drop to a new reference. After a series of pulses, on the LED D2, the voltage on C8 will reach equilibrium, so that the system will again function as described above.

It should be noted that R12 puts a slight positive voltage at the junction of R13 and R16, so that C8 always has some slight voltage on it, even if there has been no output whatever from photodiode D1, as would be the case were it disconnected from the system. The result is that if photodiode D1 were to become disconnected, the voltage at node J5-5 will still be forced into a low condition. Thus it will be seen that the system output is such that a brief low condition is indicative of the presence of a drop, and a sustained low condition is indicative either of streaming or other hazard condition, such as the disconnection of the LED D2 or photodiode D1. Consequently, a control device utilizing the present invention may, in the presence of a sustained low condition of the output of this circuit, cause the flow to be stopped and an alarm to be sounded. When flow is reinitiated, node J5-3 can be temporarily grounded in the manner discussed previously to reset C8.

The system employs a novel form of automatic gain control, by taking advantage of the fact that the voltage on C8 is indicative only of the amplified and filtered photodiode output in the absence of a drop. The naive application of automatic gain control would tend to diminish the signal-to-noise ratio of the system; however, the gain of the system is not further affected when a drop condition is present or has been detected. U1-D is a unity gain current amplifier from the output of C8 to the gate of FET Q1, which serves as a variable resistor across R5 to adjust gain of the system. R3 and C3 are optionally used to slow the action of the automatic gain control.

The 30 millisecond pulse output from U3-C may be used to drive a second LED by connection to R23 to a second transistor such as Q3. Similarly, the 15 microsecond pulse output from U3-D may gate a second gate analogous to U2-A. In this fashion, an additional drop detection circuit may be provided, and the circuit shown utilizing LED D3 and photodiode D4 is in all respects identical to the above described circuit, with node J5-4 corresponding to node J5-5, node J5-2 corresponding to node J5-3, and so forth.

Accordingly, while the invention has been described with particular reference to specific embodiments thereof, it will be understood that it may be embodied in a variety of forms diverse from those shown and described without departing from the spirit and scope of the invention as defined by the following claims.

What is claimed is:

1. A system, for detecting the presence of successive drops of fluid in a fluid drop path, comprising:
    a system input for connection to a photoelectric transducer so situated as to have a change in electrical output upon the presence of a drop in the fluid drop path;
    storage means, having an input in communication with the system input such that the input to the storage means is substantially equal to the output of the photoelectric transducer, for continuously storing and providing as an output a quantity related to the value of the photoelectric transducer output, the storage means further including gating means for gating off the storage means from the photoelectric transducer output on receiving a drop signal indicating the presence of a drop in the drop fall path so that the quantity stored and provided as an output by the storage means is related only to the value of the photoelectric transducer output in the absence of a drop; and
    comparator means, connected to the storage means and in communication with the system input, for comparing the quantity stored in the storage means with the present value of the photoelectric transducer output and for providing output related to such comparison, wherein the output from the comparator means is in communication with the storage means.

2. A system according to claim 1, wherein the quantity stored and provided as an output by the storage means is approximately representative of the last value at the storage means input stored by the storage means before the value at the storage means input has changed by more than a first threshold amount.

3. A system according to claim 1, wherein the comparator means has one input connected to the storage means input and another input connected to the storage means output, for providing a detection signal whenever the present value of the storage means input differs from the quantity at the storage means output by more than a second threshold amount.

4. A system according to claim 2, wherein the comparator means has one input connected to the storage means input and another input connected to the storage means output, for providing a detection signal whenever the present value of the storage means input differs from the quantity at the storage means output by more than a second threshold amount.

5. A system according to claim 4, further comprising sampling means, connected to the system input for providing an output of periodic samples of the photoelectric transducer output of a frequency higher than the fastest drop rate to be detected and wherein the storage means input is connected to the sampling means output so that the value at the storage means input is the sampled output of the photoelectric transducer.

6. A system according to claim 4, wherein the first and second thresholds are identical.

7. A system according to claim 5, wherein the first and second thresholds are identical.

8. A system, for detecting the presence of successive drops of fluid in a fluid drop path, comprising:
    a system input for connection to a photoelectric transducer so situated so as to have a change in electrical output on the presence of a drop in the fluid drop path;
    first means, having an input in communication with the system input, for storing and providing as an output a quantity related to the value of the photoelectric transducer output in the absence of a drop, the first means including storage means, having an input in communication with the system input, for storing and providing as an output a quantity approximately representative of the last value at the storage means input before the value at the storage means input has changed by more than a threshold amount, the storage means including a storage system and switch means, having a first side connected to the storage means input and a second side connected to the storage system and a gate connected to the comparator means output, for connecting the first and second sides thereof except when the signal on the gate is indicative of the presence of a drop, so that the storage system stores a quantity representative of the value of the photoelectric transducer output in the absence of a drop;

second means, connected to the first means and in communication with the system input, for comparing the quantity stored in the first means with the present value of the photoelectric transducer output, the second means including comparator means, having one input connected to the first means input and another input connected to the first means output, for providing a detection signal whenever the present value of the first means input differs from the quantity at the storage means output by more than the threshold amount.

9. A system according to claim 8, wherein the storage system includes a capacitor.

10. A system according to claim 2, further comprising:
automatic gain control means for automatically regulating the gain of the system so that the quantity in the storage means is approximately constant.

11. A system according to claim 9, further comprising:
automatic gain control means for regulating the gain of the system so that the voltage across the capacitor is approximately constant.

* * * * *